United States Patent
Heckele et al.

(10) Patent No.: US 8,721,525 B2
(45) Date of Patent: May 13, 2014

(54) ENDOSCOPE SYSTEM WITH A MODULATED RADIATION SOURCE

(75) Inventors: Helmut Heckele, Knittlingen (DE); Hubert Völlinger, Rastatt (DE)

(73) Assignee: Richard Wolf GmbH, Knittlingen (DE)

( * ) Notice: Subject to any disclaimer, the term of this patent is extended or adjusted under 35 U.S.C. 154(b) by 1227 days.

(21) Appl. No.: 12/023,064

(22) Filed: Jan. 31, 2008

(65) Prior Publication Data

US 2008/0188716 A1 Aug. 7, 2008

(30) Foreign Application Priority Data

Jan. 31, 2007 (EP) .................................. 07002065

(51) Int. Cl.
*A61B 1/04* (2006.01)
*A61B 1/06* (2006.01)
*G01C 3/08* (2006.01)

(52) U.S. Cl.
USPC ............ 600/111; 600/178; 600/160; 356/5.1; 356/5.01

(58) Field of Classification Search
USPC ......... 600/111, 590, 306, 475, 117, 318, 411, 600/160, 178, 182, 436, 473, 104; 356/5.1, 356/5.01; 250/268; 385/13
See application file for complete search history.

(56) References Cited

U.S. PATENT DOCUMENTS

| | | | | |
|---|---|---|---|---|
| 3,299,274 A | * | 1/1967 | Hoelter ......................... 356/217 |
| 4,415,952 A | * | 11/1983 | Hattori et al. ................. 362/572 |
| 5,534,992 A | * | 7/1996 | Takeshima et al. ............ 356/5.1 |
| 5,693,003 A | * | 12/1997 | Wolfelschneider et al. .. 600/117 |
| 5,982,555 A | * | 11/1999 | Melville et al. ............... 359/630 |
| 5,990,978 A | * | 11/1999 | Kim et al. ...................... 348/663 |
| 6,294,775 B1 | | 9/2001 | Seibel et al. |
| 2002/0040971 A1 | * | 4/2002 | Ono .......................... 250/559.38 |
| 2002/0139920 A1 | * | 10/2002 | Seibel et al. ............... 250/208.1 |
| 2003/0223053 A1 | * | 12/2003 | Liu et al. ......................... 356/5.1 |
| 2006/0034003 A1 | * | 2/2006 | Zalevsky ....................... 359/738 |
| 2007/0109505 A1 | * | 5/2007 | Kubara et al. ................... 353/69 |
| 2007/0182949 A1 | * | 8/2007 | Niclass .............................. 356/3 |
| 2008/0074552 A1 | * | 3/2008 | Jung et al. ...................... 348/663 |
| 2011/0193987 A1 | * | 8/2011 | Wong et al. ................. 348/222.1 |

FOREIGN PATENT DOCUMENTS

| | | |
|---|---|---|
| DE | 44 40 613 C1 | 7/1996 |
| EP | 1 152 261 A1 | 11/2001 |
| EP | 1 452 125 A3 | 10/2004 |
| EP | 1 622 200 A1 | 1/2008 |

OTHER PUBLICATIONS

Robert Lange et al., "Solid State Time-of-Flight Range Camera", IEEE Journal of Quantum Electronics, vol. 37, No. 3, pp. 390-397, (2001).

* cited by examiner

*Primary Examiner* — John P Leubecker
*Assistant Examiner* — Ronald D Colque
(74) *Attorney, Agent, or Firm* — Panitch Schwarze Belisario & Nadel LLP (57) ABSTRACT

An endoscope system includes a radiation source which emits a modulated radiation and is applied in a manner such that an object to be examined by an endoscope may be illuminated with the radiation. A sensor is provided for detecting the radiation reflected by the object, at at least one picture point. An evaluation device obtains readings of the detected radiation from the sensor, determines phase differences on the basis of these readings, and computes the distance of the object to the sensor device on the basis of these phase differences. A corresponding supplementary module for an endoscope and endoscope optics with these features are also provided.

12 Claims, 4 Drawing Sheets

ENDOSCOPE SYSTEM WITH A MODULATED RADIATION SOURCE

BACKGROUND OF THE INVENTION

The invention relates to an endoscope system as well as to a supplementary module for an endoscope, and to endoscope optics for measuring and/or imaging three-dimensional structures.

Endoscopes are used for carrying out visual examinations of human, animal and technical cavities, with which a three-dimensional observation of objects is possible. Video endoscopes or video cameras which are used together with an endoscope, in contrast, only permit a two-dimensional observation. It is desirable with many applications to not only to be able to see a two-dimensional image but, for example, also to be able to represent three-dimensional structures of an object to be examined.

BRIEF SUMMARY OF THE INVENTION

It is the object of the invention to provide an endoscope or endoscope system, with whose help structures may be detected and imaged in a three-dimensional manner. It is particularly desirable to provide a system for this, which may be integrated into conventional endoscopes or may be supplemented with the existing endoscope.

This object is achieved by an endoscope system for detecting three-dimensional structures, the system having at least one radiation source, which emits modulated radiation and is applied in a manner such that an object to be examined by way of the endoscope system may be illuminated with the radiation, at least one sensor for detecting the radiation reflected by the object, and an evaluation device, which obtains readings of the detected radiation from the sensor, determines phase differences at least one picture point on the basis of these readings, and computes the distance of the object to the sensor on the basis of these phase differences This object is further achieved by a supplementary module for an endoscope, which comprises an interface for connection to an endoscope, wherein the supplementary module comprises a picture observation device and a radiation source, which emits a modulated radiation which may be coupled into the endoscope via the interface, and a sensor, wherein the sensor, via the interface, may detect the modulated radiation which was reflected by an object to be examined by the endoscope, and is designed for detecting the radiation of at least one picture point, which is reflected by the object, and the sensor is connected to an evaluation device which obtains readings of the detected radiation from the sensor, determines phase differences at least one picture point on the basis of these readings, and computes the distance of the object from the sensor on the basis of these phase differences.

This object is further achieved by endoscope optics designed for application in an endoscope and which is equipped with a measurement system and comprises the following components: a radiation source, which emits a modulated radiation and may be connected to the endoscope in a manner such that an object to be examined by way of the endoscope may be illuminated with the radiation, a sensor for detecting the radiation reflected by the object at least one picture point, and an evaluation device which obtains readings of the detected radiation from the sensor, determines phase differences at the several picture points on the basis of these readings, and computes the distance of the object to the sensor on the basis of these phase differences.

The endoscope system according to one embodiment of the invention, apart from the usual components of an endoscope, comprises a radiation (beam) source which emits modulated radiation. This radiation source is arranged in the endoscope system in a manner such that an object to be examined may be illuminated with the radiation. For this, the radiation source is either arranged at the distal end of the endoscope, or however further proximally or outside the endoscope, wherein in the latter cases, a fiber-optic must be provided for leading the radiation to the distal end of the endoscope. In any case, the radiation exits at the distal end of the endoscope and radiates the object to be examined or a region of the object to be examined.

According to another embodiment of the invention, the endoscope system further comprises a sensor with one or preferably several sensor elements. The sensor or the sensor elements serve for detecting the modulated radiation which is reflected by the object. Thereby, one envisages detecting the reflected radiation at different picture points, in particular by way of several sensor elements. These correspond to different points of the object.

According to a further embodiment of the invention, an evaluation device is provided, which receives the readings generated by the sensor on account of the detected, reflected radiation, and computes the distance of the object to the sensor on the basis of these readings. Thereby, it is particularly the points of the object which correspond to individual picture points which are measured, i.e. the distance of these points to the sensor is determined. The distance measurement is effected in the evaluation device, in a manner such that in particular, with the knowledge of the modulation of the radiation source, phase differences in the radiation are determined from the readings at the individual sensor elements. One may determine the signal transfer time between the radiation source and the individual sensor elements from these phase differences. The distance may then be determined from this transfer time.

The evaluation device according to the invention, by way of the distance measurement, permits an object to be observed or examined, to be measured with regard to its three-dimensional scope. Here, preferably a certain number of picture points are detected, so that a three-dimensional image of the object may be produced.

The measurement system according to the invention may be integrated into an endoscope or an endoscope system in different manners. It is thus possible to arrange the radiation source as well as the sensor for detecting the reflected radiation, at the proximal end of the endoscope, or to arrange it connected to the proximal end, and to lead the modulated radiation to the distal end, and the reflected radiation to the proximal end via fiber-optics or optical systems in the endoscope. Alternatively, it is possible to arrange the radiation source and/or the sensor directly at the distal end of the endoscope, or in the inside of the endoscope between the proximal and the distal end. The evaluation device is preferably provided as an external component, which is connected to the radiation source and the sensor via cable. However, it is conceivable to integrate the evaluation device directly into the endoscope or into a module applied directly onto the endoscope.

The readings which the evaluation device receives from the sensor or the sensor element for the individual picture points, preferably include the radiation intensity measured at the individual picture points, in dependence on time. Here, a continuous detection and evaluation of the intensity does not need to be effected, but rather it may be sufficient to predetermine the intensity of the radiation at the individual picture points and to determine consecutive points in time, so that the phase course of the radiation may be determined at the picture points. Then, with the knowledge of the phase course or the modulation at the radiation source, one may determine the phase differences, on the basis of which one then determines the signal transfer times at the individual picture points, or in particular the differences of the transfer times between the signals at the several picture points, in order to determine the three-dimensional structure of the object.

The detection of the radiation intensity is effected according to the state of the art in a manner such that the sensor and the evaluation device are designed as a TOF-camera (time of flight), as is known, for example, from German Patent DE 44 40 613 C1 or European Patent Application Publication EP 1 622 200 A1.

The evaluation device is designed for the computation and output of the computed distance values and, as the case may be, the output of a three dimensional representation of the object. The results of the distance measurement may be selectively displayed e.g. on a monitor and the object may be represented in its three-dimensional structure for the user, additionally on a second monitor.

The endoscope system preferably comprises a common endoscope preferably a video endoscope for the transmission and representation of a picture of the object to be examined. This endoscope permits the user to observe the object to be examined (preferably continuously) on a monitor, during the measurement of this object, which may be particularly advantageous with medical applications.

Further preferably, the endoscope system comprises an endoscope with at least one optical system extending from the distal to the proximal end, which serves for the picture transmission as well as for the transmission of the modulated radiation reflected by the object. This means that the optical system on the one hand serves for transmitting a picture of the object to be examined, from the distal end of the endoscope to the proximal end of the endoscope, where for example a video camera or an eyepiece may be arranged for visual observation of the object, in the known manner. According to an embodiment of the invention, the optical system is however on the other hand also applied for leading the modulated radiation reflected by the object, from the distal end to the proximal end of the endoscope. Then, the sensor for detecting and evaluating the reflected radiation may be arranged at the proximal end.

The endoscope system further preferably comprises an endoscope with a fiber-optic which is designed for transmitting light from a light source which is arranged proximally or externally, to the distal end, wherein the light is provided for the illumination of an object to be observed by the endoscope optics. Moreover, a corresponding light source may be arranged in or at the distal end of the endoscope. The light exits at the distal end of the endoscope and illuminates the region which may be observed by the endoscope optics or the optical system.

The fiber-optic may be additional particularly preferably used for transmitting the modulated radiation from the proximal to the distal end of the endoscope, wherein the radiation then exits at the distal end. This design permits the modulated radiation to be led through the endoscope or through the endoscope shank preferably without additional elements, when the radiation source is not arranged directly at the distal end of the endoscope.

The illumination of three-dimensional structures to be observed and represented in a visual manner, is preferably effected by way of a radiation source or light source, which emits modulated light preferably in the visible range. This permits the use of the optics or optical systems and fiber-optics in conventional endoscopes, for the transmission of the modulated radiation. Thus in particular, it is possible for the measurement system according to embodiments of the invention for the three-dimensional detection of objects, to be integrated into conventional endoscopes, or to be retrofitted with conventional endoscopes.

This modulated radiation source is furthermore designed for emitting pulsed light. I.e. the light emitted by the radiation source is pulsed in a predefined clock pulse. The modulated light may for example be switched in an inactive manner for those time durations in which the video sensor is used, and thus counteract undesired influences on the color perception of the system.

For this, a clock generator is advantageously provided for the control of the radiation source and of the sensor and the evaluation device. The clock generator on the one hand sets the modulation and the pulse frequency of the emitted light. On the other hand, the clock generator also sets the clock pulse for the detection of the reflected radiation at the sensor and the subsequent evaluation. Thus, for detecting phase differences for the evaluation device, it is necessary to know the initial phase course of the radiation emitted by the radiation source, in order to then be able to determine the phase differences from the reading of the sensor or the sensor elements.

According to a preferred embodiment, common optics for transmitting a picture of the object to be examined, as well as the modulated radiation reflected by the object, are provided in the endoscope, wherein a separation device or switch-over device is arranged at the exit side of the common optics, which leads the reflected modulated radiation to the sensor, and the picture to an eyepiece or to a video sensor. The separating device or switch-over device thus serves for separating the normal picture from the reflected, modulated radiation, so that both signals may be supplied to different detection systems, specifically the modulated radiation to the sensor, and the normal picture signals to a video sensor or to an eyepiece for direct observation.

Alternatively, it is possible to provide a switch-over device which merely for the measurement by way of the sensor, briefly leads the picture or the radiation from the common optics to the sensor. This switch-over device in this context is preferably controlled by the clock generator of the radiation source. In this case, the normal picture which is visible at an eyepiece or is detected by a video sensor, is interrupted briefly for the moment of measurement. The measurement may advantageously however be effected via the sensor in a rapid manner such that this interruption may not be noticed by the human eye, and a quasi continuous picture may be provided for the observer.

According to a further preferred embodiment, the sensor according to the invention may be part of a video sensor for picture detection, or may form a construction unit with this. This means that the sensor may be integrated into a normal video sensor, which serves for the detection of the picture transmitted by the endoscope optics in the known manner. For this, memory cells with switches may be arranged for example at individual picture points, particularly preferably at all picture points such as with a TOF-camera, which permit the intensities detected by the individual sensor cells or sensor elements to be stored in the memory cells and subsequently read out for further computation. One may make do with a part device or deflection device with such a design, and it is very simply possible to integrate the measurement system according to an embodiment of the invention into the normal picture transmission or picture processing of an endoscope with the help of video technology.

A further possible embodiment of the invention envisages the sensor device for detecting the reflected modulated radiation, as well as optics or a video sensor for picture observation being integrated in a common module, which via an interface is applied on the endoscope shank on the proximal side. Thereby, the interface may be designed in a manner such that it is possible to attach the module to convention endoscopes or endoscope shanks at the proximal side, so that the measurement system may be integrated very easily into conventional endoscopes. Then ideally, only the video picture detection system attached to the endoscope at the proximal side needs to be replaced by the described module, which integrates the picture detection as well as the described measurement technology for three-dimensional detection of the object.

According to an embodiment of the invention, an illumination connection is further preferably provided, which is connected to a light source for illuminating the object and to the radiation source which emits the modulated radiation. The illumination connection may, for example at the exit side, be designed as a connection plug which is connected to the fiber-optic cable connection on the endoscope shank. This means that the illumination connection serves for coupling the radiation or the light from the radiation source into the illumination path of the endoscope, which transmits the light to the distal end of the endoscope for illuminating the object. The coupling-in location lies in the described illumination connection, which on the entry side may be connected to two radiation sources or light sources, specifically to the light source for illumination, and to the described radiation source for modulated radiation. Only one exit is provided at the exit side, which is preferably designed as a standard connection plug or standard connection coupling, which may be connected to the usual fiber-optic connections of endoscope shanks. In this manner, it is very simply possible to also use conventional endoscopes for the measurement system according to the invention, and to couple the required modulated radiation into conventional endoscopes.

As already mentioned in the preceding description, it is particularly preferable to be able to retrofit existing or conventional endoscopes in a manner such that a three-dimensional detection or measurement of the object to be examined is possible. According to an embodiment of the invention, a supplementary module for an endoscope is provided for this, which as an accessory part may be attached to endoscopes or be integrated into endoscope systems.

For this, the supplementary module comprises an interface, via which it may be attached to an endoscope and connected to this. The interface for this is preferably designed as a standard interface, in order to be able to be connected to conventional endoscope types or types of endoscope optics. A picture observation device is arranged in the supplementary module and the picture of the object region which is situated in the field of viewing of the endoscope may be detected via this device in the conventional way. For this, one may provide an eyepiece or a video sensor with a video system connecting thereto. Furthermore, a connection for an external light source is preferably provided in the supplementary module, and this light source effects the usual illumination of the region of the endoscope on the distal side. For this, the light is led from the light source, e.g. through the supplementary module to a connection plug, and via this into the fiber-optic of the endoscope. The light source may alternatively be also integrated into the supplementary module.

According to an embodiment of the invention a radiation source, particularly preferably, again a light source which emits modulated radiation and is preferably likewise connected to one or the previously mentioned connection plugs, is provided in the supplementary module. This means that the modulated radiation emitted by the radiation source is likewise led into the fiber-optic of the endoscope via the connection plug, so that the modulated radiation exits from the endoscope at the distal side, preferably together with the light for illumination.

Furthermore, the supplementary module comprises a sensor, wherein the sensor receives modulated radiation or modulated light via the endoscope/supplementary module interface, said light having been reflected by the object to be examined with the endoscope. This means that the modulated radiation is led through the fiber-optic to the distal end of the endoscope, exits there and is incident on the object. The radiation is reflected by the object and enters into the distal-side end of the endoscope optics, which leads the radiation towards the proximal end and the interface to the supplementary module. The sensor is designed for detecting the radiation reflected by the object, at one or more picture points, in the manner described above by way of the endoscope, and preferably comprises several sensor elements for this.

The sensor is connected to an evaluation device which obtains readings of the detected radiation from the sensor. The evaluation device, on the basis of these readings and in particular with the knowledge of the modulation of the radiation source, determines phase differences at the one or the several picture points or pixels, respectively, and, on the basis of these, computes the distance of the object to the sensor device. The evaluation of the radiation detected by the sensor is effected in the manner described above by way of the endoscope system. The evaluation device may be integrated into the supplementary module, but is however preferably integrated into a control device which is connected to the supplementary module which may be attached directly onto the endoscope.

It is also alternatively possible to integrate the sensory devices for three-dimensional detection of objects directly into an endoscope or into endoscope optics, which may then be inserted into an endoscope shank, in particular of a conventional endoscope. It is possible also in this manner, to retrofit present endoscopes by way of merely exchanging the endoscope optics. With this embodiment, it is essentially those elements which are integrated into the endoscope optics which were previously described by way of the supplementary module. A radiation source is further provided, which emits a modulated radiation, in particular modulated light and may be connected to the endoscope such that an object to be examined by way of the endoscope may be illuminated with the radiation. Preferably, a connection device or a connection plug is provided for this, which may be connected to the fiber-optic cable connection of an endoscope, wherein the modulated radiation as well as the light for illuminating the object may be coupled into the fiber-optic of the endoscope via the connection plug in the manner described above.

Furthermore, a sensor for detecting the radiation reflected by the object, at one or more picture points, is integrated into the endoscope optics, wherein the detection of the radiation may be effected in the manner described above. The sensor, with regard to previously mentioned design, may preferably be arranged in the endoscope at the proximal side. An arrangement at the distal end, however, is also conceivable. Given an arrangement at the proximal end of an optical system, one may also provide a separation device or switch-over device, in order to be able to separate the signal for the three-dimensional measurement, from the usual picture signal. Moreover, the already described evaluation device is provided for the endoscope optics and this device obtains readings of the detected radiation from the sensor, and determines phase differences on the basis of these readings and in particular the information on the modulation of the radiation source at the one or more picture points, and computes the distance of the object to the sensor on the basis of these phase differences. This evaluation device may either be integrated directly into the endoscope optics or it is integrated into a control device, which is connected to the endoscope optics and the sensor device arranged on it, via a lead.

It is to be understood that the preferred features described above by way of the endoscope system may also be realized in the context of the described endoscope optics and the described supplementary module.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

With regard to the endoscope system according to the invention or the additional module according to the invention or the endoscope optics according to the invention, one employs a measurement principle which is based on a TOF (time of flight) camera for the three-dimensional measurement of the object to be examined. The manner of functioning of this camera system is explained by way of FIG. 3. There, an object 2 is shown, which is observed or measured by way of the camera 4. The camera 4 comprises an illumination device 6 and a sensor 8, wherein the illumination device 6 is placed laterally of the sensor 8 essentially in a plane with this. The illumination device 6 is designed such that it emits modulated, i.e. in particular pulsed light 10 (modulated radiation). With the application in an endoscope, the pulsed light 10 preferably lies in the visible range, so that it may be transmitted via the usual optical elements in the endoscope.

Figure 3:
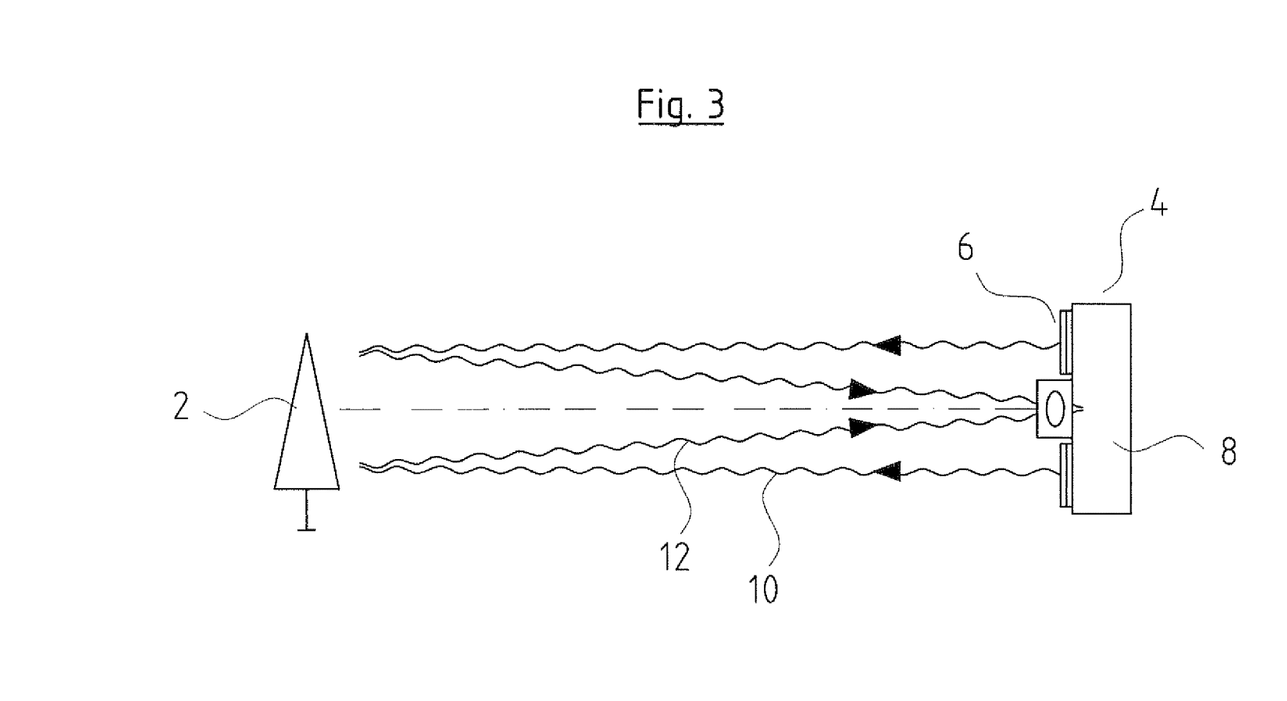
FIG. 3 is a schematic representation of the manner of functioning of a TOF-camera used in embodiments of the invention.

The pulsed light 10 is incident onto the object 2 and is sent back by this as reflected light 12 to the camera 4, and there is detected by the sensor 8 which comprises a multitude of sensor elements, of which each is allocated to an individual picture point or to a certain group of picture points, so that preferably essentially the whole object 2 is detected by the individual picture points.

The surface regions of the object 2 which face the camera 4 are distanced differently far from the camera 4 on account of the three-dimensional structure of the object 2. This leads to different transfer times of the light from the illumination device 6 back to the sensor 8. Longer transfer times of the light result for the picture points with which the object 2 or its surface is distanced further to the camera 4. The transfer time differences on account of the modulation of the emitted light 6 lead to phase differences which are detected and evaluated, in order to determine the transfer time and thus the distance of the picture points. In turn, one may then derive the three-dimensional structure of the object 2 from this. The manner of functioning of such a TOF-camera is known, for example, from DE 44 40 613 C1 or EP 1 622 200 A1.

Figure 1:
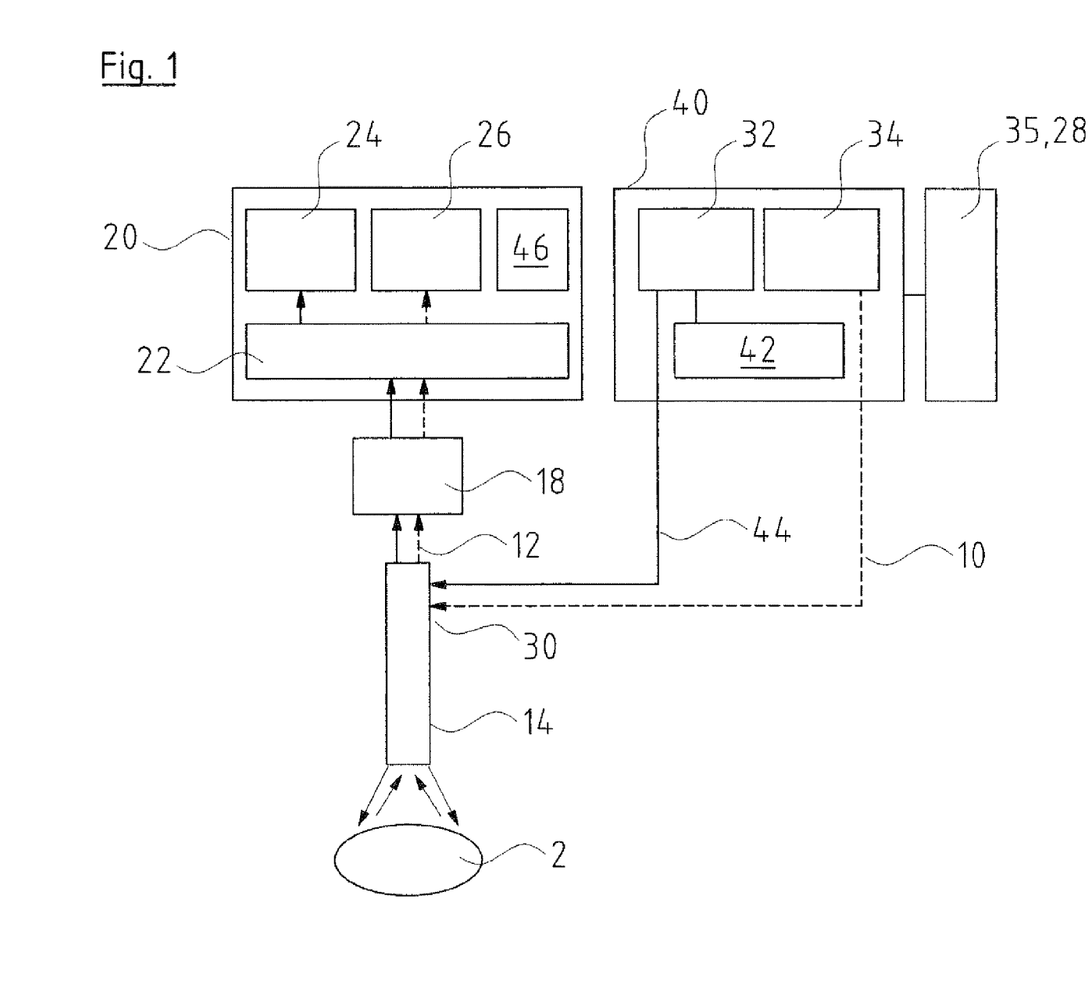
FIGS. 1 and 2 are schematic representations of the endoscope system according to an embodiment of the invention.
Figure 2:
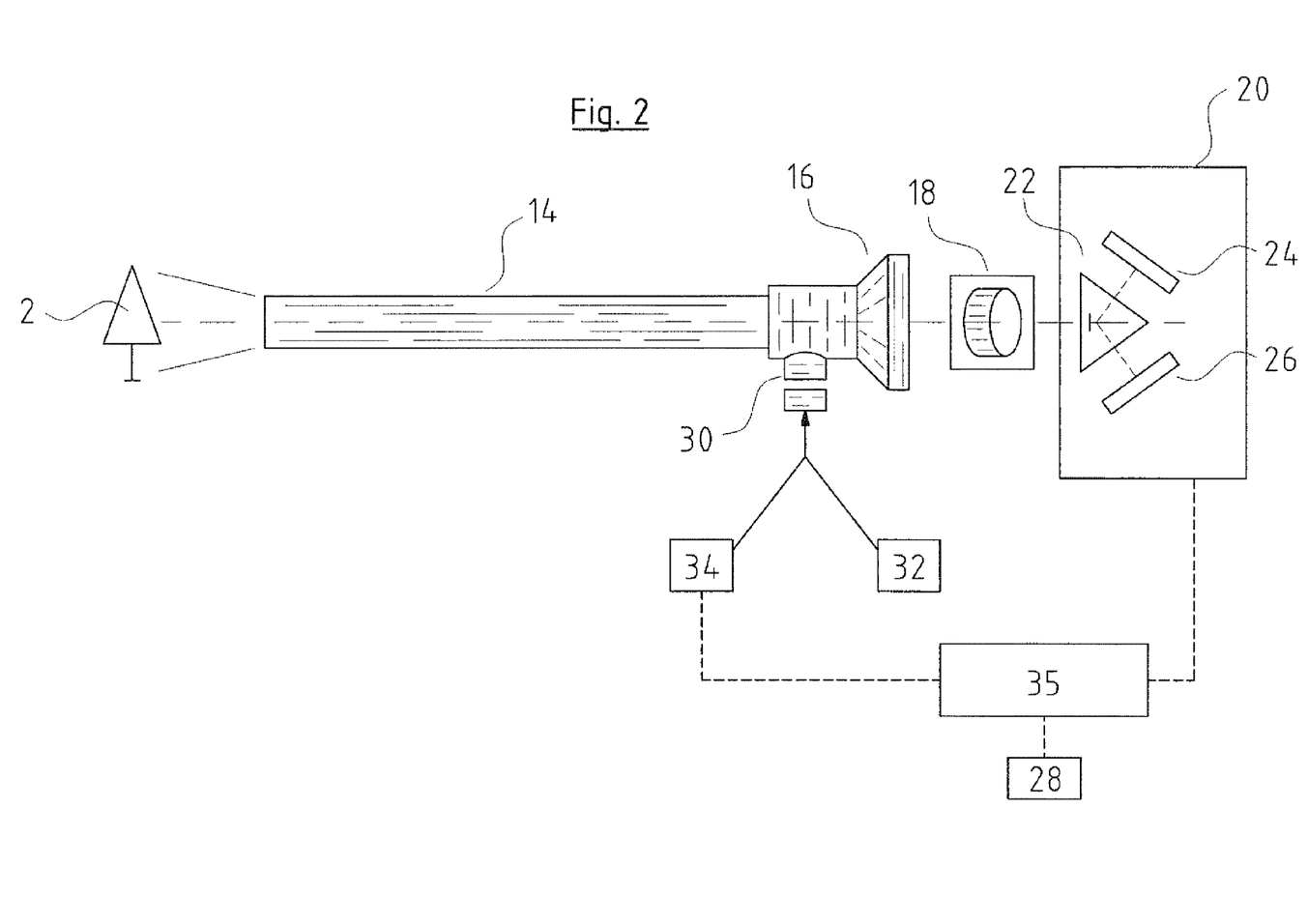

According to the invention, this measurement principle which is applied by the previously mentioned TOF-cameras, is combined with an endoscope 2 which is represented schematically in FIGS. 1 and 2. There, one uses an endoscope 14 in order to observe or examine the object 2. Thereby, the endoscope 14 is designed in a conventional manner, i.e. in its inside, it comprises in particular at least one optical system for observing the object 2, and a fiber-optic for illuminating the object 2. At the proximal side, the endoscope 14 comprises a receiver 16, to which an objective 18 as well as sensor device 20 connecting further proximally, are attached. Thereby, the objective 18 and the sensor device 20 may be grouped together in a module, preferably a supplementary module. A picture splitter 22 is provided in the sensor device 20, and this picture splitter divides the picture transmitted by the objective 18 onto for example two sensors 24 and 26, e.g. according to the manners described by FIGS. 4 to 7. The sensor 24 is designed as a conventional video sensor which detects the picture of the object 2 transmitted by the endoscope 14, which may then be brought to display on the monitor 28. The sensor 26 forms a sensor device for detecting the three-dimensional structure of the object 2 or for its measurement, and corresponds to the previously described TOF-camera 4.

The endoscope 14 in the vicinity of its proximal end, comprises a fiber-optic cable connection 30 in the usual manner, which is connected to the proximal end of a fiber-optic in the inside of the endoscope 14, which ends at the distal end. The fiber-optic cable connection 30 according to the invention, on the one hand is connected to a conventional illumination device 32 which constantly emits light for illuminating the object 2, in order to produce a picture on the sensor 24. Furthermore, a modulated radiation source or light source 34 is provided, which emits modulated or pulsed light, which is likewise fed into the fiber-optic cable connection 30. Preferably, the light emitted by the illumination device 32 as well as the light source 34 is led together in a connection component with the help of known optical elements, so that the connection component then has only one exit, which is connected to the fiber-optic cable connection 30.

The radiation source 34 as well as the sensor device 20, are connected to a control device 35. The control device 35 comprises a clock generator, which sets the clock cycle for the pulse frequency and pulse lengths of the light emitted by the radiation source 34. Furthermore, the control device 35 detects the picture signals detected by the sensor 26 and evaluates these as an evaluation unit. The clock cycle of the light emitted by the radiation source 34 is known to control device 35, so that, on detecting the reflected light, this may then determine the transfer times for individual picture points on account of the phase differences, and in this manner compute the three-dimensional structure of the object 2. This may then likewise be displayed on the monitor 28. One may alternatively also provide a separate monitor. The picture processing for the picture recorded by the sensor 24 may likewise be integrated into the control device 35. Here, a separate picture processing system may likewise be provided as an alternative.

Two sensors 24 and 26 are provided in the example shown in FIG. 2. The two functions preferably may also be integrated into a sensor, so that one may do without the picture distribution device 22.

As is shown in FIG. 1, the endoscope or the system, apart from the actual endoscope 14 with the associated objective 18, essentially consists of three modules, specifically the sensor device 20, an illumination module 40 as well as a control module, which is formed of the control device 35 and as the case may be, the monitor 28. The control module thereby may for example be formed by a personal computer as a control device 35 with an associated monitor 28. The illumination module 40 includes the illumination device 32 as well as the radiation source 34, and, as the case may be, an electronic shutter 42, for controlling or switching on and off the light emitted by the illumination device 32. The modulated radiation or the pulsed light 10, respectively, emitted by the radiation source 34, as well as the light 44 emitted by the illumination device 32, may be led to the illumination connection 30 of the endoscope 14 via separate fiber-optics. Alternatively, one may provide a common fiber-optic which connects the illumination module 40 to the fiber-optic cable connection 30, i.e. the pulsed light 10 and the light 44 were already led together in the illumination module 40 into a common light path.

Sensors 24 and 26 and, as the case may be, a picture splitter 22 as well as necessary electronic components 46 for the control or regulation of the previously mentioned components are grouped together in the sensor device 20.

The modules of the sensor device 20, the illumination module 40 as well as the control device 35, may be provided as accessory components for use with a conventional endoscope 14. Thus a convention endoscope 14 may be upgraded into an endoscope, which permits the three-dimensional detection of structures.

The possible construction and the possible function of a picture splitter 22 is explained by way of the FIGS. 4 to 7, which show four possible embodiment examples.

Figure 4:
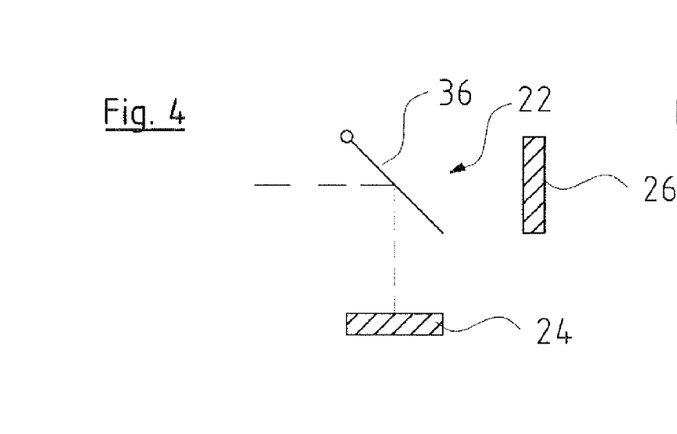
FIGS. 4 to 7 are schematic diagrams of four different possibilities of picture division.

FIG. 4 further shows a picture splitter which comprises a pivot mirror 36, which in the shown position leads the picture which exits from the optical system of the endoscope 14 or the objective 18 at the proximal side, to the sensor 24. The mirror 36 is pivoted in the direction of the arrow in FIG. 4 for the measurement by way of sensor 26, so that the beam path is no longer incident onto the sensor 24 but onto the sensor 26, and this receives the reflected, modulated radiation for the described measurement. The sensor 24 thus receives no picture at the moment of the measurement. However, the measurement may be effected so rapidly, that the mirror 36 only needs to be pivoted into the position in which the picture is guided onto the sensor 26, for a brief period of time. The interruption of the picture for the sensor 24 may be kept so short by way of this, that it is not visible to the human eye. Alternatively, the sensors 24 and 26 may also be arranged the other way round.

Figure 5:
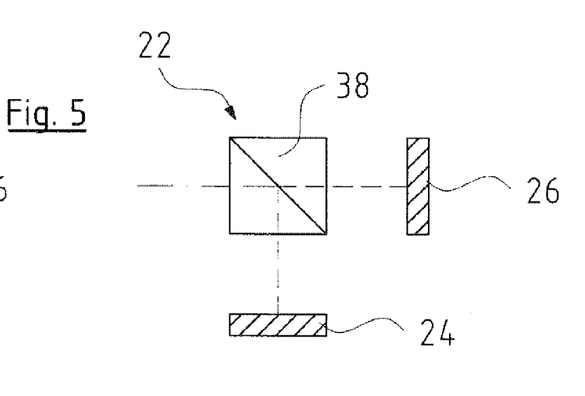

FIG. 5 shows a beam splitter 38 by way of which the light bundle exiting from the endoscope 14 at the proximal side is divided and simultaneously directed to the sensors 24 and 26. Thereby, the division is effected according to the wavelengths, so that those wavelengths which correspond to those wavelengths emitted by the radiation source 34, are deflected to the sensor 26, and all other wavelengths to the sensor 24. Thus only the sensor 26 detects the reflected modulated radiation which has been sent by the radiation source 34.

Figure 6:
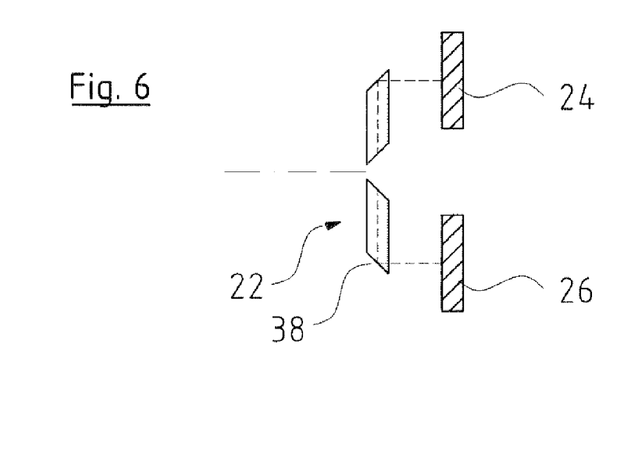
Figure 7:
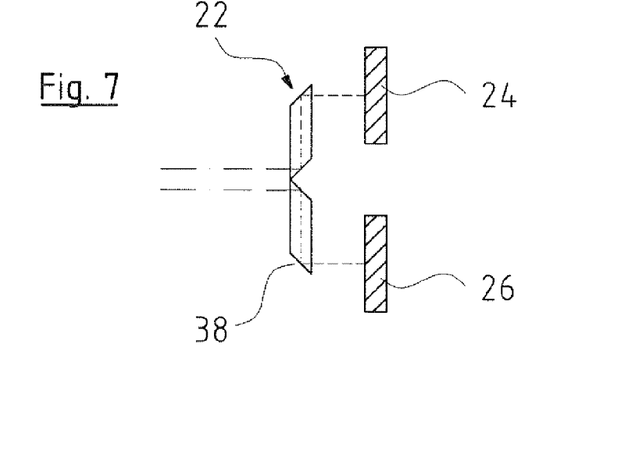

A geometric beam splitting as is shown by way of FIGS. 6 and 7, is also possible instead of a beam splitting on account of different wavelengths. With this geometric beam splitting, the light bundle exiting from the endoscope 14 at the proximal side, is geometrically divided preferably into equal parts onto the sensors 24 and 26, so that both sensors 24, 26 completely detect the complete picture and the complete wavelength spectrum. Here however, the intensity of the light at each of the sensors 24 and 26 reduces. FIG. 6 shows a single-channel geometric beam splitting; i.e. only one optics channel is provided in the endoscope. FIG. 7 shows a two-channel geometric beam splitting, with which two optics channels are provided, wherein the light of each of the two channels is distributed onto both sensors 24 and 26.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscope system for detecting three-dimensional structures, the system comprising:
 an endoscope shank having a proximal end and a distal end;
 at least one fiber-optic extending within the endoscope shank between the proximal and distal ends thereof;
 at least one radiation source (34), which emits modulated radiation led to the distal end of the endoscope shank by at least one of the at least one fiber-optic and is applied in a manner such that an object (2) to be examined by way of the endoscope system is illuminated with the modulated radiation,
 at least one sensor (26) with a plurality of sensor elements for detecting the modulated radiation reflected by the object (2) at different picture points, wherein the at least one sensor (26) forms a structural unit with a video sensor (24),
 an evaluation device (35) which obtains readings of the detected radiation from the sensor (26), determines phase differences at the different picture points, and computes a distance of the object (2) from the at least one sensor (26) based on the phase differences, and
 common optics for transmitting a picture of the object (2) to be examined and the modulated radiation reflected by the object (2), wherein a separating device or switchover device (22) is positioned between an exit side of the common optics and (i) the at least one sensor (26) and (ii) an eyepiece or the video sensor (24), and which leads the modulated radiation reflected by the object (2) to the at least one sensor (26), and the picture, to the eyepiece or to the video sensor (24).

2. The endoscope system according to claim 1, wherein the evaluation device (35) is designed for outputting computed distance values, including a three-dimensional representation of the object (2) on a monitor (28).

3. The endoscope system according to claim 1, wherein the endoscope system comprises a video endoscope for transmitting and representing a picture of the object (2) to be examined.

4. The endoscope system according to claim 1, further comprising at least one optical system extending from a distal end of the endoscope shank to a proximal end of the endoscope shank, which serves for picture transmission and for transmission of the modulated radiation reflected by the object (2).

5. The endoscope system according to claim 1, wherein at least one of the at least one fiber-optic is designed for transmission of light from a light source (32) arranged on a proximal end of the endoscope shank, to a distal end of the endoscope shank, wherein the light is provided for illuminating a region to be observed via the endoscope optics.

6. The endoscope system according to claim 1, wherein the radiation source (34) is a light source which emits modulated light in the visible range.

7. The endoscope system according to claim 1, wherein the radiation source (34) is designed for emitting pulsed light as modulated radiation.

8. The endoscope system according to claim 1, further comprising a clock generator for controlling the radiation source (34), the at least one sensor (26), and the evaluation device (35).

9. The endoscope system according to claim 1, wherein the at least one sensor (26) for detecting the reflected modulated radiation reflected by the object (2) and optics or the video sensor (24) for picture observation of the object (2) are integrated in a module (20), which is attached to the proximal side of the endoscope shank via an interface (15).

10. The endoscope system according to claim 1, futher comprising an illumination connection (30), which is connected to a light source (32) for object illumination and to the radiation source (34).

11. A supplementary module (20) for an endoscope (14) comprising an endoscope shank having a proximal end and a distal end and at least one fiber-optic extending within the endoscope shank between the proximal and distal ends thereof, the supplementary module (20) comprising:

an interface for connection to the proximal end of the endoscope shank, a picture observation device (24), a radiation source (34) coupled into the endoscope shank via the interface and emitting a modulated radiation led to the distal end of the endoscope shank by at least one of the at least one fiber-optic, at least one sensor (26), wherein the at least one sensor (26) may detect via the interface modulated radiation reflected by an object (2) to be examined by the endoscope (14), the at least one sensor being designed for detecting the radiation of different picture points reflected by the object (2), and the at least one sensor (26) is connected to an evaluation device (35) which obtains readings of the detected radiation from the sensor (26), determines phase differences at the different picture points, and computes a distance of the object (2) from the sensor (26) based on the phase differences, and common optics for transmitting a picture of the object (2) to be examined and the modulated radiation reflected by the object (2), wherein a separating device or switchover device (22) is positioned between an exit side of the common optics and (i) the at least one sensor (26) and (ii) an eyepiece or the picture observation device (24), and which leads the modulated radiation reflected by the object (2) to the at least one sensor (26), and the picture, to the eyepiece or the picture observation device (24).

12. Endoscope optics designed for application in an endoscope (14) comprising an endoscope shank having a proximal end and a distal end and at least one fiber-optic extending within the endoscope shank between the proximal and distal ends thereof, the endoscope optics being equipped with a measurement system, the endoscope optics comprising:

a radiation source (34) connected to the endoscope shank emitting a modulated radiation led to the distal end of the endoscope shank by at least one of the at least one fiber-optic such that an object (2) to be examined by the endoscope (14) is illuminated with the modulated radiation, at least one sensor (26) for detecting the modulated radiation reflected by the object (2) at different picture points wherein the at least one sensor (26) forms a structural unit with a video sensor (24), an evaluation device (35) which obtains readings of the detected radiation from the at least one sensor (26), determines phase differences at the different picture points based on these readings, and computes a distance of the object (2) from the at least one sensor (26) based on the phase differences, and common optics for transmitting a picture of the object (2) to be examined and the modulated radiation reflected by the object (2), wherein a separating device or switchover device (22) is positioned between an exit side of the common optics and (i) the at least one sensor (26) and (ii) an eyepiece or the video sensor (24), and which leads the modulated radiation reflected by the object (2) to the at least one sensor (26), and the picture, to an eyepiece or to the video sensor (24).

* * * * *